US00PP25220P2

(12) United States Plant Patent
Williams

(10) Patent No.: US PP25,220 P2
(45) Date of Patent: Jan. 6, 2015

(54) ***ALOCASIA* PLANT NAMED 'ZULU MASK'**

(50) Latin Name: ***Alocasia* hybrid**
Varietal Denomination: Zulu Mask

(71) Applicant: Brian Paul Williams, Louisville, KY (US)

(72) Inventor: Brian Paul Williams, Louisville, KY (US)

(73) Assignee: Brians Botanicals, Louisville, KY (US)

( * ) Notice: Subject to any disclaimer, the term of this patent is extended or adjusted under 35 U.S.C. 154(b) by 60 days.

(21) Appl. No.: 13/986,906

(22) Filed: Jun. 17, 2013

(51) Int. Cl.
*A01H 5/00* (2006.01)

(52) U.S. Cl.
USPC ..... Plt./373

(58) Field of Classification Search
USPC ..... Plt./373, 263.1
See application file for complete search history.

*Primary Examiner* — Kent L Bell
(74) *Attorney, Agent, or Firm* — Penny J. Aguirre

(57) ABSTRACT

A new cultivar of *Alocasia* plant named 'Zulu Mask', that is characterized by its large leaves that are dark green in color with white veins on the upper surface and dark maroon in color on the lower surface, its leaves that are long, arrow-shaped with long basal lobes and leaf tips that point downward, its leaves that are orientated horizontal to downward, its petioles that are greenish white in color, its plant height of 0.9 to 1.2 m (3 to 4 ft.) when mature, and its good resistance to root rot.

2 Drawing Sheets

Botanical classification: *Alocasia* hybrid.
Cultivar designation: 'Zulu Mask'.

BACKGROUND OF THE INVENTION

The present invention, *Alocasia* 'Zulu Mask', relates to a new and distinct interspecific hybrid of *Alocasia*, hereinafter referred to by its cultivar name, 'Zulu Mask'. 'Zulu Mask' is a new tropical plant used as a landscape and container plant.

The new cultivar was derived from a controlled breeding program conducted by the Inventor at his nursery in Louisville, Ky. The overall purpose of the breeding program is to made selections of *Alocasia* plants with large, colorful leaves that are easy to grow in the nursery and landscape and exhibit improved cold hardiness. 'Zulu Mask' arose from a cross make in June of 2009 between an unnamed plant of *Alocasia odora* as the female parent and an unnamed plant of hybrid origin from the Inventor's breeding program as the male parent. 'Zulu Mask' was selected as a single unique plant in July of 2010 from amongst the seedlings derived from the above cross.

Asexual propagation of the new cultivar was first accomplished by in vitro propagation under the direction of the Inventor in Eustis, Fla. in May of 2012. Asexual propagation by in vitro propagation of the new cultivar has shown that the unique features of the new cultivar are stable and reproduced true to type in successive generations.

SUMMARY OF THE INVENTION

The following traits have been repeatedly observed and represent the characteristics of the new cultivar. These attributes in combination distinguish 'Zulu Mask' as a new and unique cultivar of *Alocasia*.

1. 'Zulu Mask' exhibits large leaves that are dark green in color with white veins on the upper surface and dark maroon in color on the lower surface.

2. 'Zulu Mask' exhibits leaves that are long, arrow-shaped with long basal lobes and leaf tips that point downward.
3. 'Zulu Mask' exhibits petioles that are greenish white in color.
4. 'Zulu Mask' exhibits a plant height of 0.9 to 1.2 m (3 to 4 ft.) when mature.
5. 'Zulu Mask' exhibits leaves that are orientated horizontal to downward.
6. 'Zulu Mask' exhibits good resistance to root rot.

The female parent of 'Zulu Mask', an unnamed plant of *Alocasia odora*, differs from 'Zulu Mask' in being taller in height (up to 2.5 m), in having petioles that are green in color, and in having leaves that are held upright and are green in color on both surfaces with green veins. The male parent of 'Zulu Mask', an unnamed plant from the Inventor's breeding program, differs from 'Zulu Mask' in having leaves with basal lobes that are shorter (less deeply cut), in being shorter in height, in being more sensitive to cold and less resistant to root rot. 'Zulu Mask' can be most closely compared to the cultivars *Alocasia macrorrhiza* 'Lutea' (not patented) and *Alocasia* 'Amazonica' (not patented). 'Lutea' is similar to 'Zulu Mask' in having large leaves but differs from 'Zulu Mask' in having leaves that are green on both surfaces with yellow veins on the upper surface, and in being more cold sensitive. 'Amazonica' is similar to 'Zulu Mask' in having foliage that is green with white veins on the upper surface. 'Amazonica' differs from 'Zulu Mask' in having leaves with rippled margins, and in being shorter in height, more cold sensitive, and highly susceptible to root rot.

BRIEF DESCRIPTION OF THE DRAWING

The accompanying colored photographs illustrate the overall appearance and distinct characteristics of the new *Alocasia*, 'Zulu Mask'. The photographs were taken of a 2 year-old plant of 'Zulu Mask' as grown outdoors in a 2-gallon container under 6 mm poly and natural lighting in Louisville, Ky.

Figure 1:
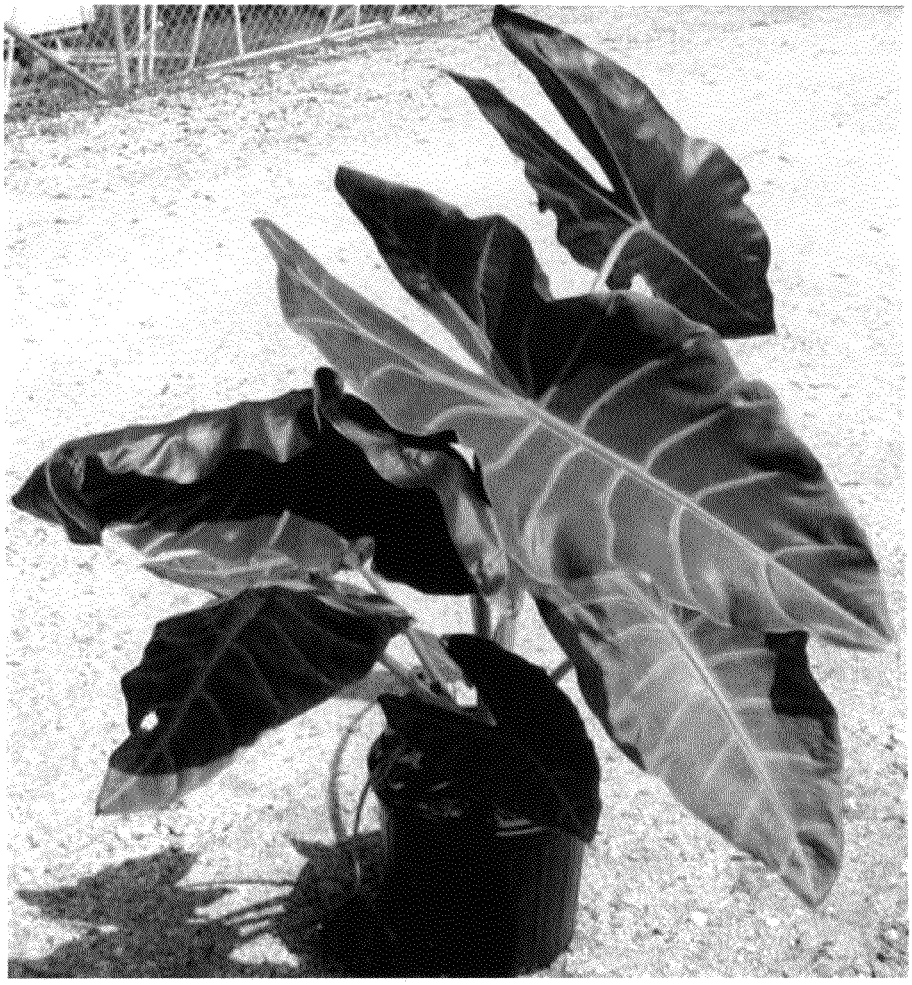
FIG. 1 provides an overall view of the foliage and plant habit of 'Zulu Mask'.
Figure 2:
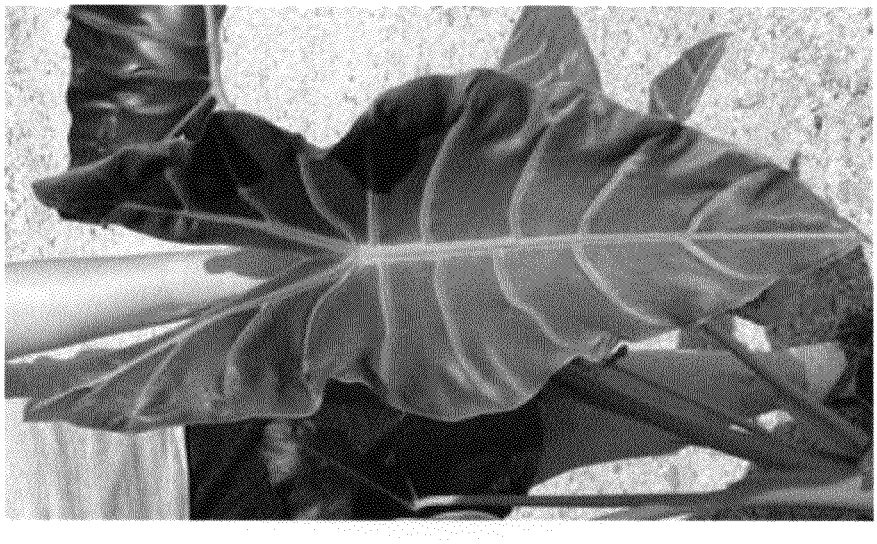

The photograph in FIG. 2 provides a close-up view of the upper surface of a leaf of 'Zulu Mask'.

Figure 3:
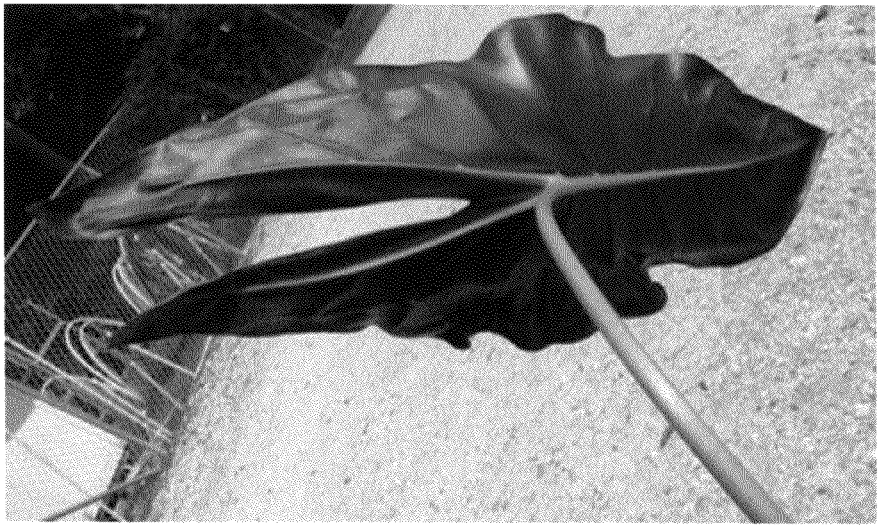

The photograph in FIG. 3 provides a close-up view of the lower surface of a leaf of 'Zulu Mask'.

The colors in the photographs are as close as possible with the photographic and printing technology utilized and the color values cited in the Detailed Botanical Description accurately describe the colors of the new *Alocasia*.

DETAILED BOTANICAL DESCRIPTION OF THE PLANT

The following is a detailed description of three year-old plants of the new cultivar as grown outdoors in full sun under 2 mm poly greenhouse plastic in Louisville, Ky. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Plant type*.—Tropical perennial herb.

*Plant habit*.—Upright, stemless.

*Height and spread*.—Reaches about 0.9 to 1.2 m in height and width (3 to 4 ft.).

*Cold hardiness*.—At least to U.S.D.A. Zone 8.

*Diseases and pests*.—Has shown good resistance to root rot.

*Roots*.—Fleshy.

*Propagation type*.—In vitro propagation is preferred.

*Growth rate*.—Vigorous.

*Stem description*.—Stemless.

Foliage description:

*Leaf shape*.—Cordate-sagittate.

*Leaf division*.—Single.

*Leaf base*.—Sagittate, deeply cut; lobes about 20 to 30.5 cm in length and 7.6 to 12.7 cm in width.

*Leaf apex*.—Cuspidate with tip downward.

*Leaf venation*.—Pinnate, color: upper mature surfaces; 157C, lower mature lower surface; matches leaf surface with mid rib that branches in lobes 193A.

*Leaf margins*.—Slightly undulate.

*Leaf attachment*.—Petiolate.

*Leaf arrangement*.—Alternate.

*Leaf surface*.—Upper surface and lower surface; coriaceous, glabrous and satiny.

*Leaf orientation*.—Held horizontal to downward when mature.

*Leaf color*.—Young upper surface a blend of 144A and 137A, young lower surface; 144A and suffused with N77A, mature foliage: upper surface; 137C and turning to N137A, lower surface; N77A.

*Leaf size*.—Up to 0.9 m in length and about 30 cm in width.

*Petioles*.—Held erect to semi-erect, about 61 cm in length and 1.3 cm in distal diameter and about 5.1 cm in diameter near base, glabrous surface, 145D in color with tiny spots of N77A and blending with 161D near base, tuber-like trunk; formed at the base of the petioles with age, about 30.5 cm in length and 10.2 cm in width on a 3 year-old plant, comprised of petiole scales, surface is rough and paper-like, color is a blend of 165A and 165C.

Inflorescence description: Blooms were not formed on the plants available for data collection.

It is claimed:

1. A new and distinct cultivar of *Alocasia* plant named 'Zulu Mask' as herein illustrated and described.

* * * * *